(12) United States Patent
Brandstadt et al.

(10) Patent No.: US 7,205,373 B2
(45) Date of Patent: *Apr. 17, 2007

(54) ENZYME CATALYZED ORGANOSILICON ESTERS AND AMIDES

(75) Inventors: Kurt Friedrich Brandstadt, Frankenmuth, MI (US); Thomas Howard Lane, Midland, MI (US); Richard A. Gross, Plainview, NY (US)

(73) Assignees: Dow Corning Corporation, Midland, MI (US); Polytechnic University, Brooklyn, NY (US)

( * ) Notice: Subject to any disclaimer, the term of this patent is extended or adjusted under 35 U.S.C. 154(b) by 469 days.

This patent is subject to a terminal disclaimer.

(21) Appl. No.: 10/642,098

(22) Filed: Aug. 15, 2003

(65) Prior Publication Data
US 2004/0082024 A1    Apr. 29, 2004

Related U.S. Application Data

(60) Provisional application No. 60/403,960, filed on Aug. 16, 2002, provisional application No. 60/403,962, filed on Aug. 16, 2002.

(51) Int. Cl.
*C08G 77/14* (2006.01)
(52) U.S. Cl. .......................... 528/26; 528/41; 556/439; 556/440
(58) Field of Classification Search .............. 528/26, 528/41; 556/439, 440
See application file for complete search history.

(56) References Cited

U.S. PATENT DOCUMENTS

| | | | | |
|---|---|---|---|---|
| 3,119,855 A | * | 1/1964 | Bailey et al. | 556/436 |
| 4,587,320 A | * | 5/1986 | Swihart | 528/23 |
| 5,239,085 A | * | 8/1993 | Enami et al. | 549/215 |
| 5,891,977 A | | 4/1999 | Dietz et al. | |
| 5,914,420 A | * | 6/1999 | Buese et al. | 556/448 |
| 5,981,743 A | | 11/1999 | Gross et al. | |
| 6,133,466 A | * | 10/2000 | Edelmann et al. | 556/440 |
| 6,288,129 B1 | | 9/2001 | Gruning et al. | |

FOREIGN PATENT DOCUMENTS

JP           J04262794          9/1991

OTHER PUBLICATIONS

Qiu et al., Lipase-catalyzed bioconversion of organosilyl alcohol in microaquous phase, Huanan Ligong Daxue Xuebo, Ziran Kexueban, Jan. 1, 1997, pp. 51-54.
Zong et al., Esterification of organosilyl alcohol catalyzed by lipase in organic phase, Gongye Weishengwu, vol. 28, Issue 4, Jan. 1, 1998, pp. 17-20.
Zong et al., Enhancement of lipase-catalyzed esterification in organic solvent by ultrasonic irradiation, Huanan Ligong Daxue Xuebao, Ziran Kxueban, vol. 28, No. 3, Jan. 1, 2000, pp. 101-104.
Qiu et al., Lipase from *Candida cylindracea* catalyzed organosilicon alcohol esterification in organic solvent, Gongye Weishengwu, vol. 27, Issue 3, Jan. 1, 1997, pp. 16-19.
Aouf et al., Preparation and enzymic cleavage of chiral acetoxymethyl- and hydroxymethylsilanes, Phosphorus, Sulfur Silicon Relat. Elem. vol. 88, Issue 1-4, Jan. 1, 1994, pp. 207-215.
Qiu et al., Abstract: Influence of water content on *C. cylindracea* lipase-catalyzed bioconversion of organosilicon compounds, Guizhou Gongye Daxue Xuebao, vol. 27, Issue 4, Jan. 1, 1998, pp. 91-96.
Qiu et al., Abstract: Interesterification of trimethylsilyl alcohol catalyzed by *C cylindracea* lipase in organic medium, Guizhou Gongye Xuebao, Ziran Kexueban, vol. 28, Issue 5, Jan. 1, 1999, pp. 79-83.
Burgess et al., Enantioselective Esterifications of Unsaturated Alcohols Mediated by a Lipase Prepared from *Pseudomonas* sp., J. Am. Chem. Soc. 1991, 113, pp. 6129-6139.
Sparks et al., Lipase Mediated Resolution of Chiral (E)-Vinylsilanes: An Improved Procedure for the Production of (R)- and (S)-(E)-1-Trialkylsilyl-1-Buten-3-OL Deriviatives, Tetahedron Letters, vol. 32, No. 33, 1991, pp. 4085-4088.
Davoli et al., A Novel Approach to a Precursor of the Carbapenem Antibiotic PS-5 Via Aziridine Stereospecific Carbonylation, Heterocycles, vol. 53, No. 11, 2000, pp. 2379-2389.
Gill et al., Lipase-Silicone Biocomposites: Efficient and Versatile Immobilized Biocatalysts, Journal of the American Chemical Society, vol. 121, No. 41, Oct. 20, 1999, pp. 9487-9496.
Luisi, Enzymes Hosted in Reverse Micelles in Hydrocarbon Solution, Angewandte Chemie, International Edition in English, vol. 24, No. 6, Jun. 1985, pp. 439-450.
Hood et al., Polyester Resin Synthesis Techniques For Achieving Lower VOC And Improved Coating Performance, Journal of Coatings Technology, vol. 58, No. 739, Aug. 1986, pp. 49-52.
Kawamoto et al., Enzymatic Preparation of Optically Active Silicon-Containing Amino Acids and Their Application, Applied Biochemistry and Biotechnology, vol. 88, 2000, pp. 17-22.
Kawamoto et al., Efficient optical resolution of 2-(4-chlorophenoxy) propanoic acid with lipase by the use of organosilicon compounds as substrate: the role of silicon atom in enzymatic recognition, Journal of Biotechnology, 18, 1991, pp. 85-92.

(Continued)

*Primary Examiner*—Margaret G. Moore
(74) *Attorney, Agent, or Firm*—Dinsmore & Shohl LLP

(57) ABSTRACT

Methods for forming organosilicon esters and amides are provided. Additionally, organosilicon esters and amides are provided. The organosilicon esters and amides may be formed by contacting a hydrolase enzyme with an organosilicon reactant and an organic reactant. The enzyme may catalyze the formation of an ester bond between carboxylic acid, ester, or amide functional groups of the organosilicon or organic reactant and alcohol functional groups of the organic or organosilicon reactant. The enzyme may catalyze the formation of an amide bond between carboxylic acid, ester, or amide functional groups of the organosilicon or organic reactant and amine functional groups of the organic or organosilicon reactant.

5 Claims, 13 Drawing Sheets

OTHER PUBLICATIONS

Fukui et al., Enzymatic Preparation of Optically Active Silylmethanol Derivatives Having A Stereogenic Silicon Atom by Hydrolase-catalyzed Enantioselective Esterification, Tetrahedron: Asymmetry, vol. 5, No. 1, 1994, pp. 73-82.

Uejima et al., Efficient kinetic resolution of organosilicon compounds by stereoselective esterification with hydrolases in organic solvent, Appl Microbiol Biotechnol, 1993, 38, pp. 482-486.

Gross et al., Polymer Synthesis by In Vitro Enzyme Catalysis, Chem Rev., 2001, 101, pp. 2097-2124.

Tanaka, Chapter 1 Biochemical Approach Biochemical Reactions in Organic Solvents, Kagaku, Zokan 1991, 119, pp. 63-71.

Adelhorst et al., Enzyme Catalysed Preparation of 6-O-Acylglucopyranosides, Synthesis, Feb. 1990, pp. 112-115.

Merget et al., Biocatalysis in Preparative Organosilicon Chemistry: Microbial Reduction of rac-1-(4-Fluorophenyl)-1-methyl-1-sila-2-cyclohexanone and Microbial Hydrolysis of rac-(SiS, CR/SiR, CS)-2-Acetoxy-1-(4-flluorophenyl)-1-methyl-1-silacyclohexane, Biocatalysis in Preparative Organosilicon Chemistry, pp. 27-32.

Kobayashi et al., Enzymatic Polymerization, Chem. Rev. 2001, 101, pp. 3793-3818.

Zong et al., Bioconversion of organosilicon compounds by horse liver alcohol dehydrogenase: the role of the silicon atom in enzymatic reactions, Appl Microbiol Biotechnol, 1991, 36, pp. 40-43.

Tsuji et al., Enantioselective dehydrogenation of β-hydroxysilanes by horse liver alcohol dehydrogenase with a novel in-situ NAD+ regeneration system, Appl Microbiol Biotechnol, 1994, 41, pp. 219-224.

Yamanaka et al., Enzymatic preparation of optically active 3-trimethylsilylalanine, Appl Microbiol Biotechnol, 1996, 45, pp. 51-55.

Tsuji et al., Enzymatic preparation of D-p-trimethylsilylphenylalanine, Appl Microbiol Biotechnol, 1997, 47, pp. 114-119.

Kawamoto et al., Enzymatic Conversion of Organosilicon Compounds in Organic Solvents, Methods in Biotechnology, vol. 15: Enzymes in nonaqueous solvents: Methods and Protocols, Humana Press, Inc., Totowa NJ, 2001, pp. 339-355.

Braunmuhl et al., Enzymatic Grafting of Amylose from Poly(dimethylsiloxanes), Macromolecules, 1995, 28, pp. 17-24.

Braunmuhl et al., Polydimethylsiloxanes With Amylose Side Chains by Enzymatic Polymerization, Macromol. Symp. 103, 1996, pp. 141-148.

Kawamoto et al., Efficient Enzymatic Synthesis of Amide with (Aminomethyl)trimethylsilane, Journal of Bioscience and Bioengineering, vol. 87, No. 5, pp. 607-610.

Klibanov, Enzymatic catalysis in anhydrous organic solvents, TIBS 14, Apr. 1989, pp. 141-144.

Tanaka et al., Organosilicon Biochemistry, Annals New York Academy of Sciences, 1990, 613, (Enzyme Eng. 10), pp. 702-706.

Tanaka, Seeking possibilities of enzymes—Biochemical conversion of organosilicon compounds, Nippon Oyo Koso Kyokaishi, 1994, 28, pp. 10-17.

Reetz et al., Efficient Immobilization of Lipases by Entrapment in Hydrophobic Sol-Gel Materials, Biotechnology and Bioengineering, vol. 49, 1996, pp. 527-534.

Ishikawa et al., Enzymatic synthesis of silicon-containing dipeptides with 3-trimethylsilylalanine, Appl Microbiol Biotechnol, 1999, 51, pp. 470-473.

Bjorkling et al., A Highly Selective Enzyme-catalysed Esterification of Simple Glucosides, J. Chem. Soc., Chem. Commun., 1989 pp. 934-935.

Kumar et al., Synthesis of novel Silicon-based Macromers and Polymers by Enzymatic Catalysis, Polymeric materials: Science & Engineering 2003, 88, pp. 429-430.

* cited by examiner

ENZYME CATALYZED ORGANOSILICON ESTERS AND AMIDES

CROSS REFERENCE TO RELATED APPLICATIONS

This application claims priority to U.S. Provisional Application Nos. 60/403,960 and 60/403,962, filed Aug. 16, 2002.

BACKGROUND OF THE INVENTION

The present invention relates to the formation of organosilicon esters and amides and more specifically, to the formation of organosilicon esters and amides using an enzymatic route and to the organosilicon esters and amides formed thereby.

Ester and polyester compounds may be synthesized with an acid or base catalyst at high temperatures for long periods. Although these reaction conditions favor the equilibrium of polycondensation, they also promote uncontrolled side reactions, redistribution of monomers sequences, cross linking, and broad molecular weight distributions. Additionally, the typical acid and base catalysts are not regioselective and may catalyze esterification at all reactive groups on a polyfunctional monomer. The acid and base catalysts may cause the decomposition of potentially useful functional groups, such as epoxy groups, and bonds, such as siloxane bonds. Thus, the ability to control the material structure is essentially lost.

Traditional methods of synthesizing amide compounds may not be selective. For example, the methods may not be regioselective and/or enantioselective. Therefore, methods of synthesizing amides may not provide the ability to control the material structure.

Thus, the need remains in the relevant art for improved methods of forming structurally defined organosilicon esters and amides, and the need remains in the relevant art for more structurally defined organosilicon esters and amides.

SUMMARY OF THE INVENTION

In accordance with an embodiment of the present invention, a method of forming an organosilicon ester is provided. The method comprises contacting a hydrolase enzyme with an organosilicon reactant and an organic reactant. The organosilicon reactant comprises an organosilicon having the formula

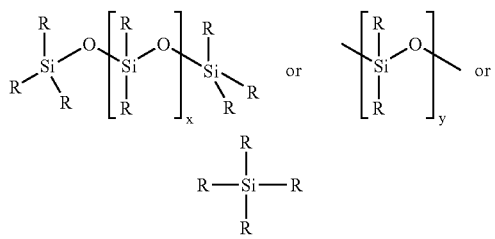

wherein:
each R is independently selected from alkyl, haloalkyl, unsaturated alkyl, aryl, hydroxy, alkoxy, hydrogen, —(OSiR$_2$)$_x$—OSiR$_3$, or R';
at least one of R=R'';
x is 0 or greater than 0;
y is equal to or greater than 3; and
R' is:

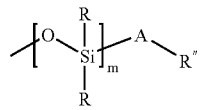

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
R'' is independently carboxylic acid, ester, amide, or alcohol; and
m is 0 or greater than 0.

The organic reactant comprises an organic molecule having at least one carboxylic acid functional group, ester functional group, amide functional group, or alcohol functional group, and combinations thereof. The at least one functional group of the organic reactant comprises carboxylic acid, ester, or amide when R'' is alcohol, and the at least one functional group of the organic reactant comprises alcohol when R'' is carboxylic acid, ester, or amide. The enzyme catalyzes the formation of an ester bond between carboxylic acid, ester, or amide functional groups of the organosilicon reactant or the organic reactant and alcohol functional groups of the organosilicon reactant or the organic reactant to form the organosilicon ester.

In accordance with another embodiment of the present invention, a method of forming an organosilicon ester is provided. The method comprises contacting a hydrolase enzyme with an organosilicon reactant and an organic reactant. The organosilicon reactant comprises an organosilicon having the formula

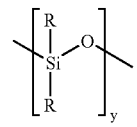

wherein:
each R is independently selected from alkyl, haloalkyl, unsaturated alkyl, aryl, hydroxy, alkoxy, hydrogen, —(OSiR$_2$)$_x$—OSiR$_3$, or R';
at least one of R=R'';
y is equal to or greater than 3; and
R' is:

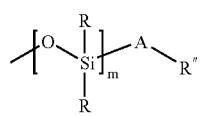

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;

R" is independently carboxylic acid, ester, amide, or alcohol; and m is 0 or greater than 0.

The organic reactant comprises an organic molecule having at least one carboxylic acid functional group, ester functional group, amide functional group, or alcohol functional group, and combinations thereof. The at least one functional group of the organic reactant comprises carboxylic acid, ester, or amide when R" is alcohol, and the at least one functional group of the organic reactant comprises alcohol when R" is carboxylic acid, ester, or amide. The enzyme catalyzes the formation of an ester bond between carboxylic acid, ester, or amide functional groups of the organosilicon reactant or the organic reactant and alcohol functional groups of the organosilicon reactant or the organic reactant to form the organosilicon ester.

In accordance with a further embodiment of the present invention, a method of forming an organosilicon amide is provided. The method comprises contacting a hydrolase enzyme with an organosilicon reactant and an organic reactant. The organosilicon reactant comprises an organosilicon having the formula

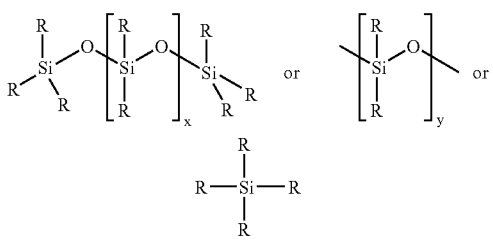

wherein:
each R is independently selected from alkyl, haloalkyl, unsaturated alkyl, aryl, hydroxy, alkoxy, hydrogen, —(OSiR$_2$)$_x$—OSiR$_3$, or R';
at least one of R=R';
x is 0 or greater than 0;
y is equal to or greater than 3; and
R' is:

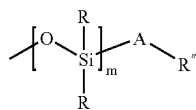

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
R" is independently carboxylic acid, ester, amine, or amide; and
m is 0 or greater than 0.

The organic reactant comprises an organic molecule having at least one carboxylic acid functional group, ester functional group, amine functional group, or amide functional group, and combinations thereof. The at least one functional group of the organic reactant comprises carboxylic acid, ester, or amide when R" is amine, and the at least one functional group of the organic reactant comprises amine when R" is carboxylic acid, ester, or amide. The enzyme catalyzes the formation of an amide bond between carboxylic acid, ester, or amide functional groups of the organosilicon reactant or the organic reactant and amine functional groups of the organosilicon reactant or the organic reactant to form the organosilicon amide.

In accordance with another embodiment of the present invention, a method of forming an organosilicon amide is provided. The method comprises contacting a hydrolase enzyme with an organosilicon reactant and an organic reactant. The organosilicon reactant comprises an organosilicon having the formula

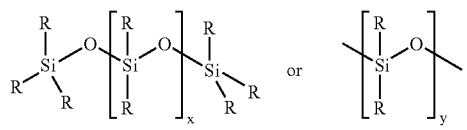

wherein:
each R is independently selected from alkyl, haloalkyl, unsaturated alkyl, aryl, hydroxy, alkoxy, hydrogen, —(OSiR$_2$)$_x$—OSiR$_3$, or R';
at least one of R=R";
x is 0 or greater than 0;
y is equal to or greater than 3; and
R' is:

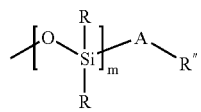

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
R" is independently carboxylic acid, ester, amine, or amide; and
m is 0 or greater than 0.

The organic reactant comprises an organic molecule having at least one carboxylic acid functional group, ester functional group, amine functional group, or amide functional group, and combinations thereof. The at least one functional group of the organic reactant comprises carboxylic acid, ester, or amide when R" is amine, and the at least one functional group of the organic reactant comprises amine when R" is carboxylic acid, ester, or amide. The enzyme catalyzes the formation of an amide bond between carboxylic acid, ester, or amide functional groups of the organosilicon reactant or the organic reactant and amine functional groups of the organosilicon reactant or the organic reactant to form the organosilicon amide.

In accordance with another embodiment of present invention, an organosilicon ester is provided. The organosilicon ester comprises a structurally defined compound having the formula:

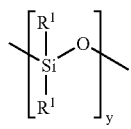

wherein:
each $R^1$ is independently selected from alkyl, haloalkyl, unsaturated alkyl, aryl, hydroxy, alkoxy, hydrogen, $-(OSiR^1{}_2)_x-OSiR^1{}_3$, or R'";
at least one of $R^1 = R'''$;
y is equal to or greater than 3; and
R'" is:

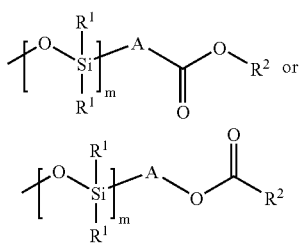

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
$R^2$ is an organic compound; and
m is 0 or greater than 0.

In accordance with an embodiment of the present invention, an organosilicon amide is provided. The organosilicon amide comprises a structurally defined compound having the formula:

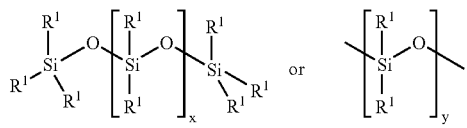

wherein:
each $R^1$ is independently selected from alkyl, haloalkyl, unsaturated alkyl, aryl, hydroxy, alkoxy, hydrogen, $-(OSiR^1{}_2)_x-OSiR^1{}_3$, or R'";
at least one of $R^1 = R'''$;
x is 0 or greater than 0;
y is equal to or greater than 3; and
R'" is:

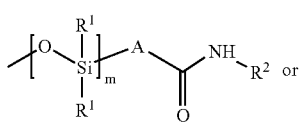

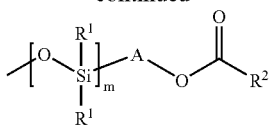

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
$R^2$ is an organic compound; and
m is 0 or greater than 0.

DETAILED DESCRIPTION OF THE PREFERRED EMBODIMENTS

Figure 1:
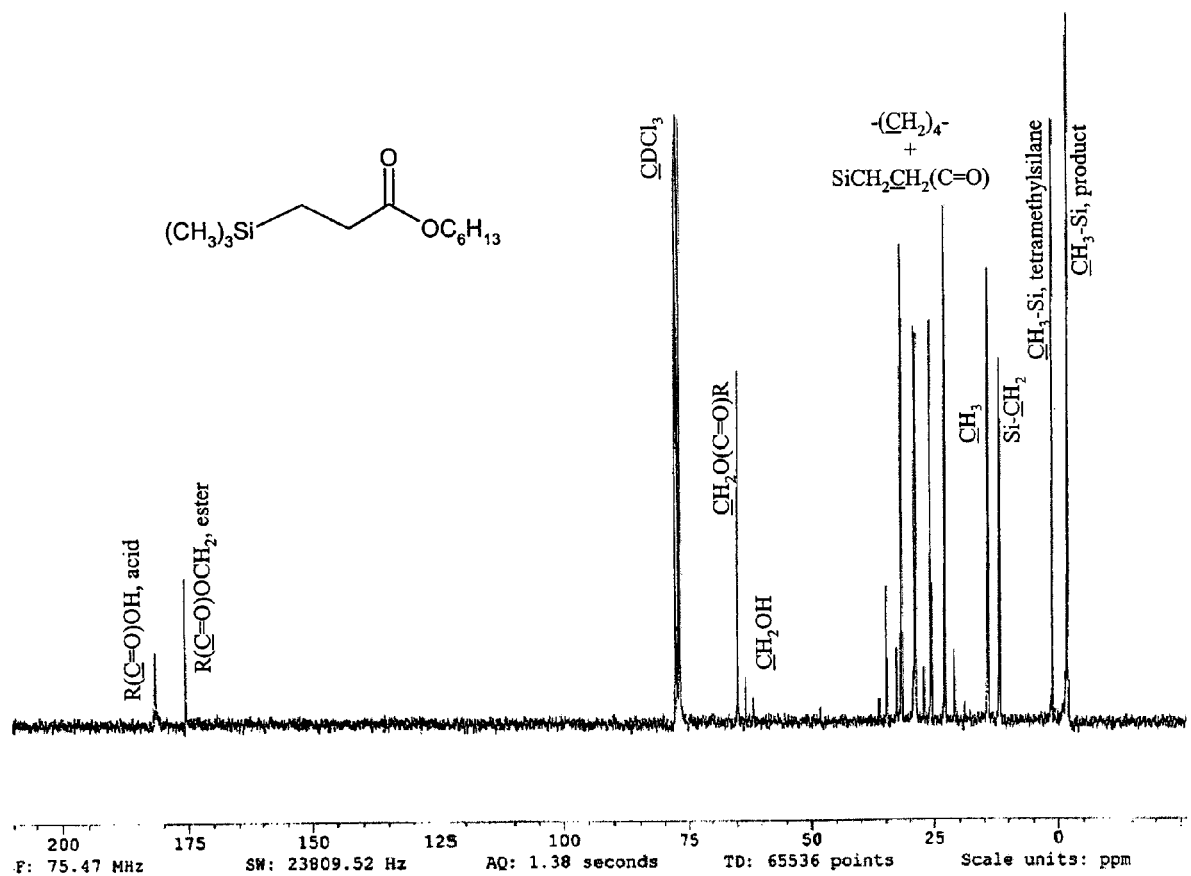
FIG. 1 is a $^{13}C$ DEPT NMR spectrum of the esterification of Example 1.

The present invention utilizes hydrolase enzymes to form novel organosilicon esters and amides under mild reaction conditions.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The present invention relates to the reaction of an organosilicon reactant and an organic reactant in the presence of a hydrolase enzyme to form organosilicon esters and amides. The reaction involves the formation of an ester bond between at least one carboxylic acid, ester, or amide functional group and at least one alcohol functional group. Alternatively, the reaction involves the formation of an amide bond between at least one carboxylic acid or ester functional group and at least one amine functional group or between an amide functional group and an amine functional group as shown in the reaction sequences below:

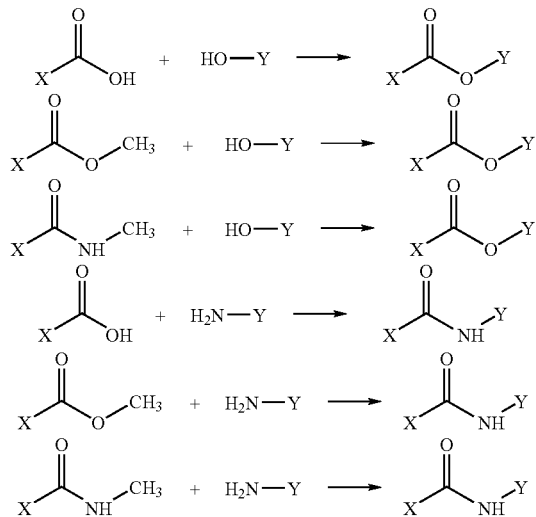

In the above reactions, X and Y represent a portion of an organosilicon or an organic compound other than the carboxylic acid, ester, alcohol, amine, or amide functional groups. It will be understood that the ester or amide functional groups are not limited to the methylated ester or amide as shown in the above reactions. Rather, the ester or amide functional group may have any desired group substituted for the methyl group shown.

The organosilicon reactant is an organosilicon species. The organosilicon reactant may be a silane or may have at least one siloxane bond. The organosilicon reactant has at least one carboxylic acid, ester, alcohol, amine, or amide functional group, and the organosilicon reactant may be monofunctional or polyfunctional. The carboxylic acid, ester, alcohol, amine, or amide functional groups may be pendant, terminal, or be in any other suitable location. However, the carboxylic acid, ester, alcohol, amine, or amide functional groups may not be directly bonded to the silicon. The organosilicon reactant may be linear, branched, resinous, or cyclic. Suitable linear, branched, or resinous organosilicon reactants having at least one siloxane bond generally correspond to Formula (I), suitable cyclic organosilicon reactants having at least three siloxane bonds generally correspond to Formula (II), and suitable silane reactants generally correspond to Formula (III), as shown below:

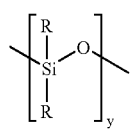

wherein:
each R is independently selected from alkyl, haloalkyl, unsaturated alkyl, aryl, hydroxy, alkoxy, hydrogen, —(OSiR$_2$)$_x$—OSiR$_3$, or R';
at least one R=R';
x is 0 or greater than 0;
y is equal to or greater than 3; and
R' is:

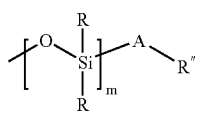

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
R" is independently carboxylic acid, ester, amide, amine, or alcohol; and
m is 0 or greater than 0.

In accordance with an embodiment of the present invention, x may be between 0 to about 250. The organosilicon reactant may be selected such that y is between about 3 to about 6. The organosilicon reactant may be selected such that A is a C$_3$ to C$_{20}$ hydrocarbon, and m may be between 0 and about 250.

It will be understood by those skilled in the art that the portion of the organosilicon structure shown within the brackets of Formulas (I) and (II) do not have to be identical repeating units. Rather, the R groups may be independently chosen for each of the repeating units. It will be understood that alkyl, haloalkyl, unsaturated alkyl, alkoxy, and hydrocarbon may be substituents having one carbon or more than one carbon. It will be further understood that when A is a substituted hydrocarbon the substitutions may be in the middle of the carbon chain or pendant on the carbon chain. However, the substitution will not generally be terminal on the end of the carbon chain next to R". The organosilicon reactants of Formulas (I), (II), and (III) are acceptable substrates that allow the hydrolase enzyme to selectively catalyze the esterification or amidation reaction at the reactive sites of the organosilicon reactant. The reactive sites of the organosilicon reactant comprise the carboxylic acid, ester, amide, alcohol, or amine functional groups.

Organic reactants useful in the present invention generally have a carboxylic acid, ester, alcohol, amine, or amide functional group, or a combination thereof. The organic reactants may be linear, branched, or cyclic organic molecules, and they may be monofunctional or polyfunctional and saturated or unsaturated. The carboxylic acid, ester, alcohol, amine, or amide functional groups may be pendant, terminal, or be in any other suitable location. Additionally, the organic reactant may be an organosilicon. Examples of suitable organic reactants include, but are not limited to, hexanol, 2-hydroxyethylmethacrylate, hexanediol, polyethylene glycol, adipic acid, hexyl amine, octanoic acid, phenyl acetic acid methyl ester, dimethyl adipate, and tetramine.

Generally, the at least one functional group of the organic reactant comprises an alcohol functional group or amine functional group when at least one of R" of Formulas (I–III) comprises carboxylic acid, ester, or amide. The at least one functional group of the organic reactant comprises a carboxylic acid functional group, ester functional group, or amide functional group when at least one of R" of Formulas (I–III) comprise alcohol or amine. It will be understood that the organic reactant may have more than one functional group, and it will be further understood that the functional groups may be the same functional group or different functional groups.

In accordance with an embodiment of the present invention, the organic reactant may be in a liquid form, and a liquid-to-liquid reaction may occur between the organic reactant and the organosilicon reactant. Thus, the reaction may occur in bulk. In accordance with another embodiment of the present invention, the organic reactant or organosilicon reactant may be a solid and the reaction may be between a liquid and a solid. When the organic reactant or organosilicon reactant is in the form of a solid, the reactions of the present invention may occur on the surface of the solid. Thus, the surface of the solids may be modified.

The organosilicon reactant and the organic reactant are contacted with a hydrolase enzyme in order to catalyze the formation of the amide or ester bond. It will be understood that the organosilicon and organic reactant may be contacted with the hydrolase enzyme sequentially. The hydrolase enzyme is generally an esterase, lipase, or protease and combinations thereof, and the hydrolase enzyme is more generally lipase or protease. The hydrolase enzyme may be derived from a bacterial, fungal, or mammalian source, or the hydrolase enzyme may be derived from any other suitable source. For example, the hydrolase enzyme may be Novozyme 435® (N435) lipase available from Novozyme (Bagsvaerd, Denmark), *Candida cylindricia* lipase type VII (CCL) available from Sigma (St. Louis, Mo.), porcine pancreatic lipase (PPL) available from Sigma (St. Louis, Mo.), and protease enzymes such as subtilisin and papain available from Sigma (St. Louis, Mo.). The enzyme is generally present as a heterogeneous suspension, and the enzyme may be lyophilized or immobilized.

The hydrolase enzyme catalyzes the formation of an ester bond between a carboxylic acid, ester, or amide functional group and an alcohol functional group in a one-step reaction. Alternatively, the hydrolase enzyme catalyzes the formation of an amide bond between a carboxylic acid or an ester functional group and an amine functional group in a one-step reaction. Additionally, the hydrolase enzyme catalyzes the formation of an amide bond between an amine functional group and an amide functional group. Thus, the enzyme catalyzes the formation of an ester bond between carboxylic acid, ester, or amide functional groups of the organosilicon reactant or the organic reactant and alcohol functional groups of the organic reactant or the organosilicon reactant to form the organosilicon ester. Alternatively, the enzyme catalyzes the formation of an amide bond between the carboxylic acid, ester, or amide functional groups of the organosilicon reactant or the organic reactant and amine functional groups of the organic reactant or the organosilicon reactant to form the organosilicon amide.

In accordance with an embodiment of the present invention, the organosilicon ester may be a structurally defined compound of the formula:

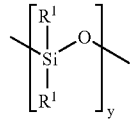

Formula (IV)

wherein:

each $R^1$ is independently selected from alkyl, haloalkyl, unsaturated alkyl, aryl, hydroxy, alkoxy, hydrogen, —$(OSiR^1_2)_x$—$OSiR^1_3$, or $R'''$;

at least one of $R^1$=$R'''$;

y is equal to or greater than 3; and $R'''$ is:

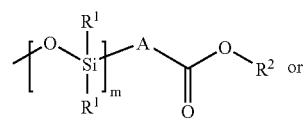

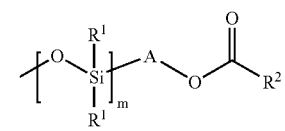

wherein:

A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;

$R^2$ is an organic compound; and m is 0 or greater than 0.

In accordance with an embodiment of the present invention, the organosilicon amide may be a structurally defined compound of the formula:

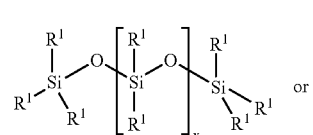

Formula (V)

or

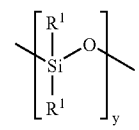

Formula (VI)

wherein:

each $R^1$ is independently selected from alkyl, haloalkyl, unsaturated alkyl, aryl, hydroxy, alkoxy, hydrogen, —$(OSiR^1_2)_x$—$OSiR^1_3$, or $R'''$;

at least one of $R^1$=$R'''$;

y is equal to or greater than 3; and

R''' is:

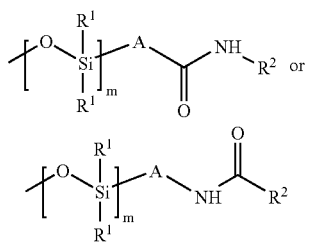

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;
$R^2$ is an organic compound; and
m is 0 or greater than 0.

It will be apparent to those having skill in the art that more than one functional group may be present on an organosilicon reactant and/or on an organic reactant. Therefore, organosilicon ester or amide monomers, macromers, and polymers may be formed using the enzymatic method of the present invention. For example, the polymers may be of the -AABB- variety wherein AA represents an organosilicon reactant having two functional groups (AA) and BB represents an organic reactant having two functional groups (BB) that react to form ester or amide bonds. Alternatively, the polymers may be of the terpolymer type or any other suitable type of polymer. Additionally, the polymers may be crosslinked in any suitable manner.

The hydrolase enzyme selectively catalyzes the formation of the amide or ester bonds. For example, the hydrolase enzyme may be regioselective or enantioselective, or combinations of both. Thus, structurally defined organosilicon amides and esters may be formed in accordance with the present invention.

When an interfacial enzyme is used, the organosilicon reactants appear to enhance the rate of esterification or amidation catalyzed by the enzyme in comparison to the rate of esterification or amidation catalyzed by the enzyme when organic materials are used in place of organosilicon materials. Lipase is an example of an interfacial enzyme. Thus, the use of organosilicon reactants may be advantageous in forming organic materials containing ester or amide bonds.

The reactions are generally carried out under mild reaction conditions. The temperature of the reactions is generally between about 20° C. and 100° C., and the reaction is more generally carried out at a temperature of between about 40° C. to about 70° C. No acid or base catalysts are required. The reactions may be performed under solventless (neat) conditions, or the reactions may be performed utilizing a solvent. Suitable solvents include, but are not limited to, hexane, toluene, xylene, and other hydrophobic alkyl or aromatic organic solvents.

The ability to synthesize organosilicon esters and amides under mild reaction conditions is advantageous because the mild reaction conditions do not cleave the siloxane bonds of the siloxane reactants. Therefore, novel organosilicon esters and amides may be synthesized. Additionally, the various functional groups of the organosilicon and organic reactants may be chosen to introduce a desired functionality into the resulting organosilicon ester or amide. For example, a hydrophobic organosilicon and a hydrophilic organic may be chosen such that the resulting organosilicon ester or amide is an amphiphilic molecule having desired surfactant properties. Alternatively, phenol functional groups may be chosen and then selectively coupled after the formation of the organosilicon ester or amide to synthesize an electrically conductive organosilicon ester or amide. Fibers, films, coatings, gels and other materials may be synthesized using this enzymatic route having desired properties such as, for example, adhesiveness and the ability to self assemble.

In order that the invention may be more readily understood, reference is made to the following examples, which are intended to be illustrative of the invention, but are not intended to be limiting in scope.

EXAMPLE 1

Novozyme 435 (N435), *Candida cylindricia* (CCL), and porcine pancreatic (PPL) lipase were used to catalyze the esterification of trimethylsilylpropionic acid with hexanol as shown in the following diagram:

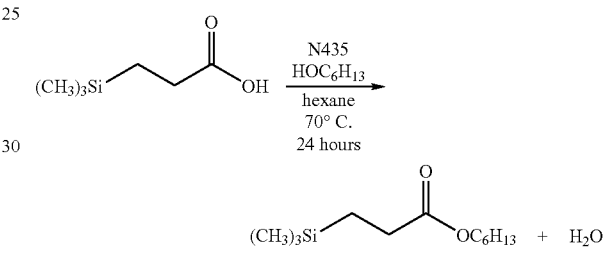

The reactions were conducted with constant stirring (i.e. magnetic stir bar) in a two-neck round-bottom flask attached to a Dean-Stark trap and a water-cooled condenser in a heated oil bath. The reactions were performed in refluxing hexane (i.e. 70° C. pot, 90° C. bath temperature). The organic reactant was added to the organosilicon-solvent solution at 70° C. After homogenization, the dried enzyme was added to the reaction mixture and the reactions were conducted for 24 hours. The reactions were formulated with organosilicon:organic and solvent:monomer mole ratios equal to 1:1 and 10:1, respectively. The enzyme:monomer weight ratio was 1:10. The lipases formed heterogeneous suspensions in the stirred organic mixtures. In the presence of the Dean-Stark trap, the formation of a hexane-water azeotrope further promoted the esterification reactions.

Figure 2:
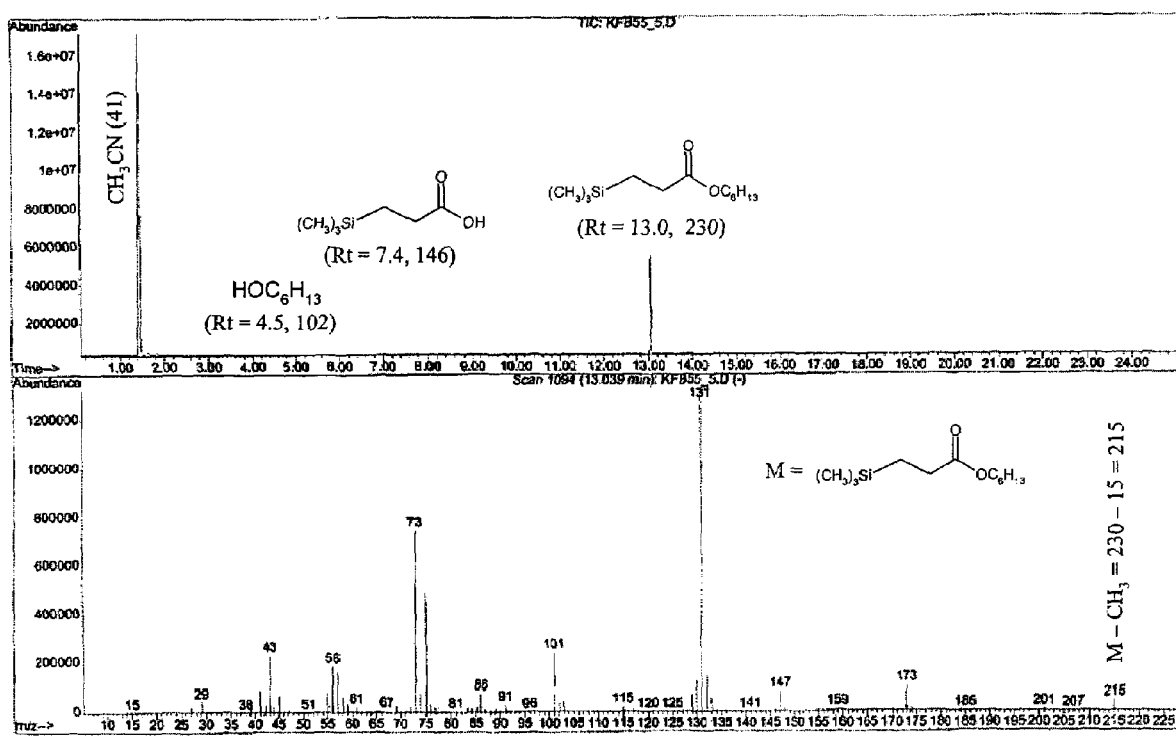
FIG. 2 is a GC MS of the esterification of Example 1.

After the reaction, chloroform (~10 mL) was added to the mixture to remove the contents from the flask and filter out the enzyme. Subsequently, the filtrate was evaporated on a rotary evaporator and dried in a vacuum oven overnight at ~45° C. in order to isolate the product. The reactions were characterized by $^1$H and $^{13}$C nuclear magnetic resonance spectroscopy (NMR), gas chromatography-mass spectrometry (GC-MS), gas chromatography—flame ionization detection (GC-FID), and electrospray mass spectrometry (ESI MS). FIG. 1 illustrates the $^{13}$C NMR of the esterification. FIG. 2 illustrates the GC-MS of the esterification. Based on the analyses, lipase was observed to catalyze the esterification reaction. Comparatively, N435 was determined to be more active than CCL or PPL. The materials were observed to contain a mixture of products and reactants.

EXAMPLE 2

N435, CCL, and PPL were used to catalyze the esterification of 1,3-bis(3-carboxypropyl)tetramethyldisiloxane (i.e., diacid disiloxane) with hexanol as shown in the following diagram:

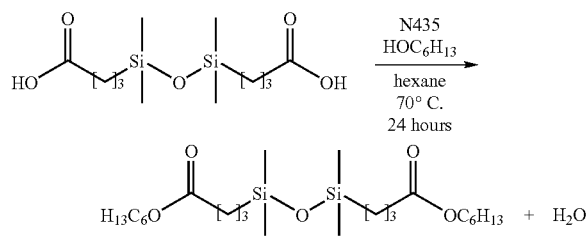

The reactions were conducted with constant stirring (i.e. magnetic stir bar) in a two-neck round-bottom flask attached to a Dean-Stark trap and a water-cooled condenser in a heated oil bath. The reactions were performed in refluxing hexane. The organic reactant was added to the organosilicon-solvent solution at 70° C. After homogenization, dried lipase enzyme was added to the reaction mixture and the reactions were conducted for 24 hours. The reactions were formulated with organosilicon:organic and solvent:monomer mole ratios equal to 1:1 and 10:1, respectively. The enzyme:monomer weight ratio was 1:10. In the presence of the Dean-Stark trap, the formation of a hexane-water azeotrope further promoted the esterification reactions.

Figure 3:
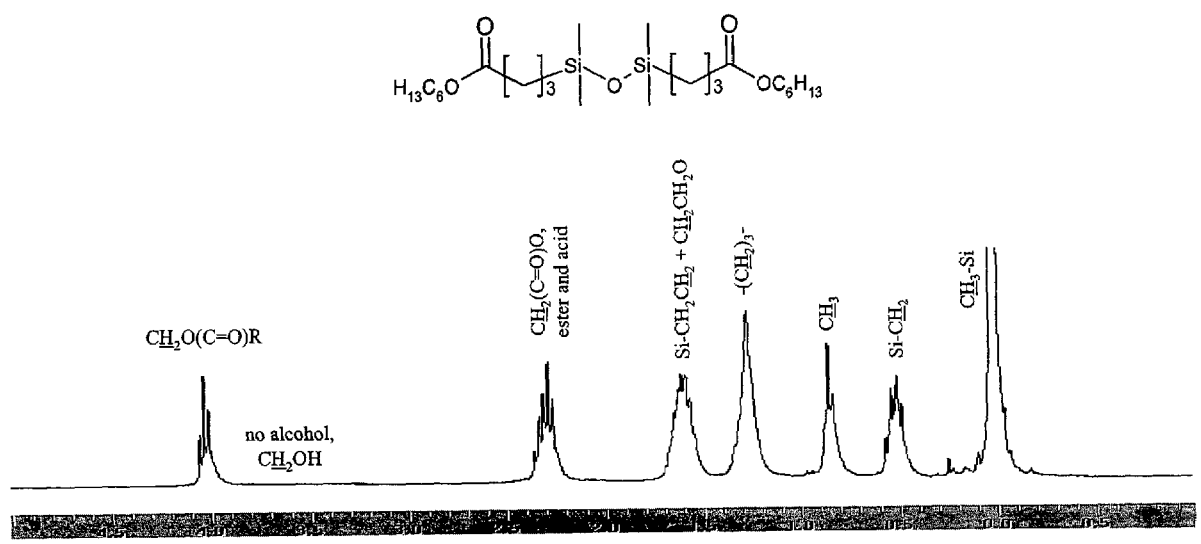
FIG. 3 is a $^1H$ NMR spectrum of the esterification of Example 2.
Figure 4:
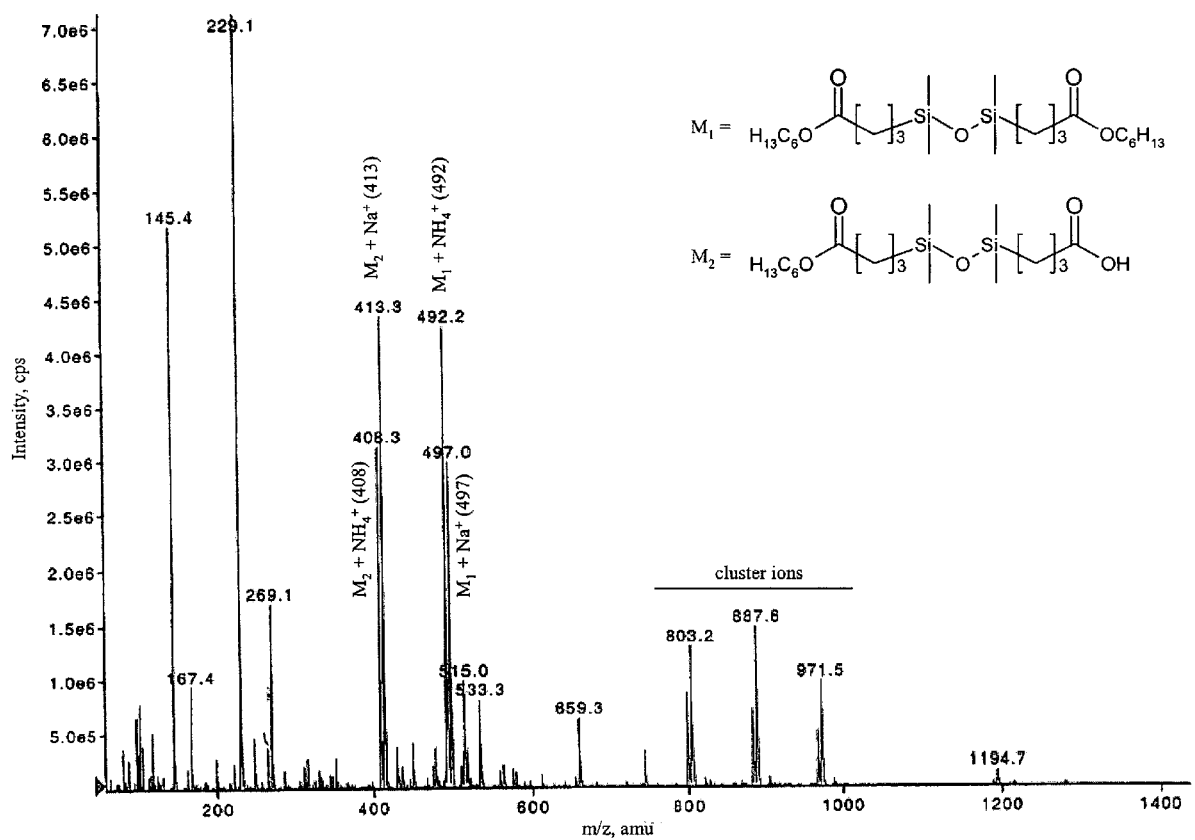
FIG. 4 is an ESI MS of the esterification of Example 2.

After the reaction, chloroform (~10 mL) was added to the mixture to remove the contents from the flask and filter out the enzyme. Subsequently, the filtrate was evaporated on a rotary evaporator and dried in a vacuum oven overnight at ~45° C. in order to isolate the product. The reactions were characterized by $^1$H and $^{13}$C NMR, GC-MS, GC-FID, and ESI MS. FIG. 3 illustrates the $^1$H NMR of the esterification. FIG. 4 illustrates the ESI MS of the esterification. Based on the analyses, lipase was observed to catalyze the esterification reaction. Comparatively, N435 was determined to be more active than CCL or PPL. The materials were observed to contain a mixture of products and reactants.

EXAMPLE 3

N435 was used to react the diacid disiloxane of Example 2 with 2-hydroxyethylmethacrylate (HEMA) in refluxing hexane or neat at 70° C. for 1 hour as shown in the following diagram:

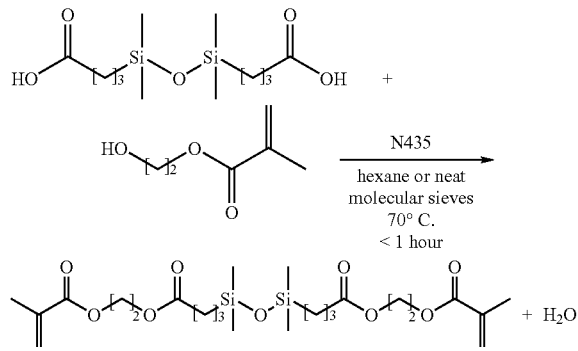

The reactions were conducted with constant stirring (i.e. magnetic stir bar) in a two-neck round-bottom flask attached to a Dean-Stark trap and a water-cooled condenser in a heated oil bath. The reactions were formulated with organosilicon:organic and solvent:monomer mole ratios equal to 1:2 and 10:1, respectively. The enzyme:monomer weight ratio was 1:10. In addition to the Dean-Stark trap, molecular sieves (i.e. sieve:enzyme weight ratio=2:1) were used to adsorb water in order to further promote the esterification reaction.

After the reaction, chloroform (~10 mL) was added to the mixture to remove the contents from the flask and filter out the enzyme. Subsequently, the filtrate was evaporated on a rotary evaporator and dried in a vacuum oven overnight at ~45° C. in order to isolate the product.

Figure 5:
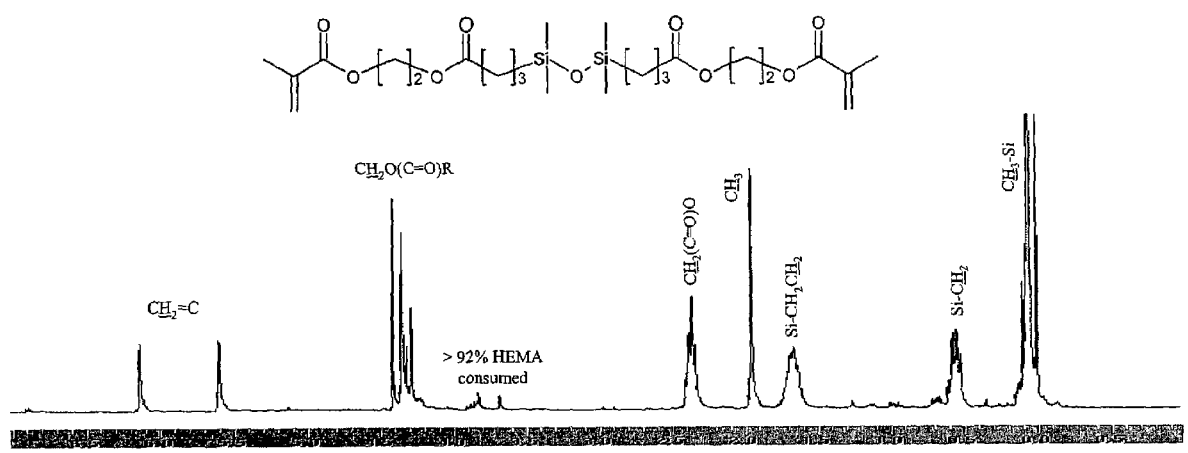
FIG. 5 is a $^1H$ NMR spectrum of the esterification of Example 3.
Figure 6:
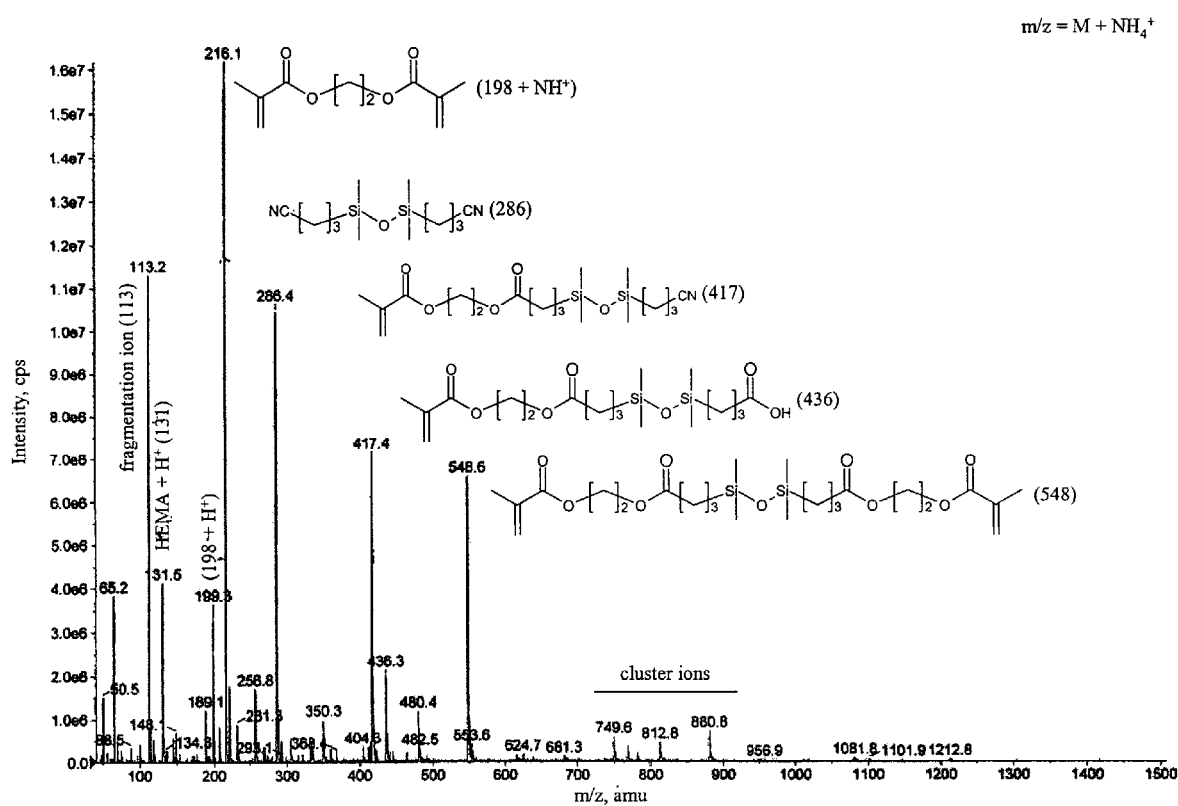
FIG. 6 is an ESI MS of the esterification of Example 3.

In hexane and neat media, 82% and 91% of the HEMA was consumed within 1 hour, respectively. In the presence of molecular sieves, aliquots of the reaction were analyzed by $^1$H NMR every 5 minutes. Based on the spectral data, HEMA was nearly consumed within the first 5 minutes. After 1 hour, the neat reaction was filtered and dried to isolate a crude oily product. The product was characterized by $^1$H and $^{13}$C NMR, ESI MS, Fourier transform infrared spectroscopy (FTIR), and gel permeation chromatography-refractive index detection (GPC-RI). FIG. 5 illustrates the $^1$H NMR of the esterification. FIG. 6 illustrates the ESI MS of the esterification. Based on the molecular characterization, the material was observed to contain a mixture of mono- and di-ester products and reactants.

EXAMPLE 4

An organosilicon polyester was synthesized by reacting a diacid disiloxane (AA) and hexanediol (BB) with N435 in refluxing hexane at 70° C. for 6 days as shown in the diagram below:

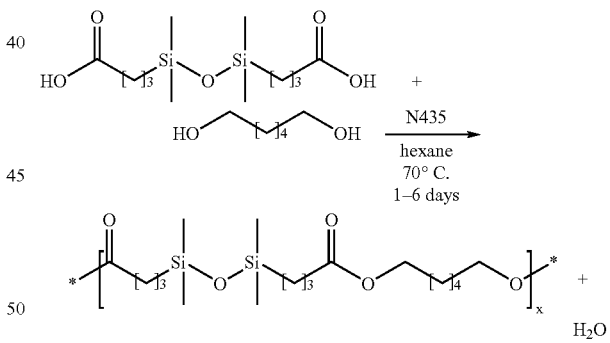

The reaction was conducted with constant stirring (i.e. magnetic stir bar) in a two-neck round-bottom flask attached to a Dean-Stark trap and a water-cooled condenser in a heated oil bath. The reaction was formulated with organosilicon:organic and solvent:monomer mole ratios equal to 1:1 and 10:1, respectively. The enzyme:monomer weight ratio was 1:10. The use of the Dean-Stark trap further promoted the esterification reaction.

Figure 7:
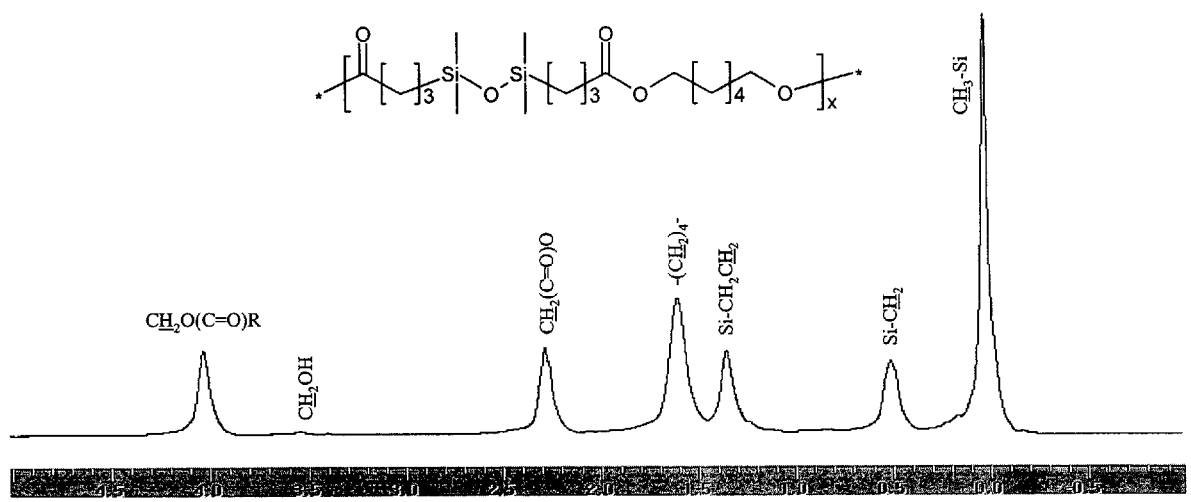
FIG. 7 is a $^1H$ NMR spectrum of the esterification of Example 4.

The progress of the reaction was monitored by $^1$H NMR. After 6 days, the mixture was filtered, evaporated, and dried to isolate an oily product. The material was characterized by $^1$H, $^{13}$C, and $^{29}$Si NMR, matrix-assisted laser desorption/ionization time-of-flight mass spectrometry (MALDI-TOF MS), FTIR, GPC-RI, thermal gravimetric analysis (TGA), and differential scanning calorimetry (DSC). FIG. 7 illustrates the ¹H NMR of the esterification.

The material was observed to contain, primarily, linear as well as cyclic -[AABB]$_x$- organosilicon polyesters. No residual diacid disiloxane was observed. Based on the GPC-RI results, the Mn and Mw values were 5140 and 15710, respectively, with a 3.1 polydisperity. Based on the thermal analysis, the material experienced a critical mass loss at 381° C. vs. 164° C. (i.e. diacid disiloxane reactant). The Tg was measured to be −80° C. In comparison to the diacid disiloxane (Tg=−76° C.), similar amounts of energy were required to achieve molecular motion. During the DSC heating cycles, crystalline phases (Tm) were observed at −47° C. & −38° C. (0.7 J/g), and 92° C. (0.9 J/g). A cold crystallization (Tcc=−15° C., 50.4 J/g) and two crystalline phases (Tm=30° C., 45 J/g; 46° C., 8.6 J/g) were detected in the diacid disiloxane.

EXAMPLE 5

An organosilicon polyester was synthesized by reacting a diacid-endblocked polydimethylsiloxane (diacid PDMS, AA) and polyethylene glycol (BB) with N435 in refluxing hexane at 70° C. for 6 days as shown in the following diagram:

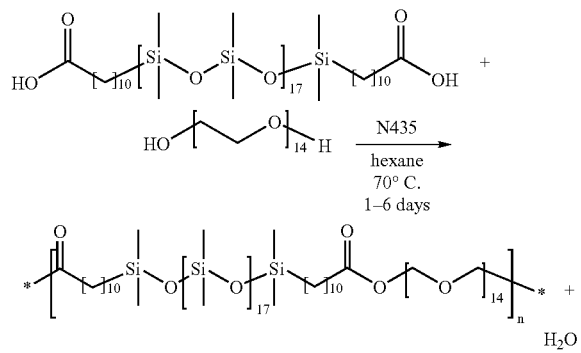

The reaction was conducted with constant stirring (i.e. magnetic stir bar) in a two-neck round-bottom flask attached to a Dean-Stark trap and a water-cooled condenser in a heated oil bath. The reaction was formulated with organosilicon:organic and solvent:monomer mole ratios equal to 1:1 and 10:1, respectively. The enzyme:monomer weight ratio was 1:10. The use of the Dean-Stark trap further promoted the esterification reaction.

The progress of the diacid PDMS esterification was monitored by ¹H NMR. Based on the spectral data, N435 was observed to catalyze the formation of ester bonds (i.e., -[AABB]$_x$-) with large polymeric substrates over 4 days.

EXAMPLE 6

N435 was used to catalyze the polyesterification of a carbinol-endblocked polydimethylsiloxane (diol PDMS, BB) and adipic acid (AA) in refluxing hexane at 70° C. for 6 days as shown in the following diagram:

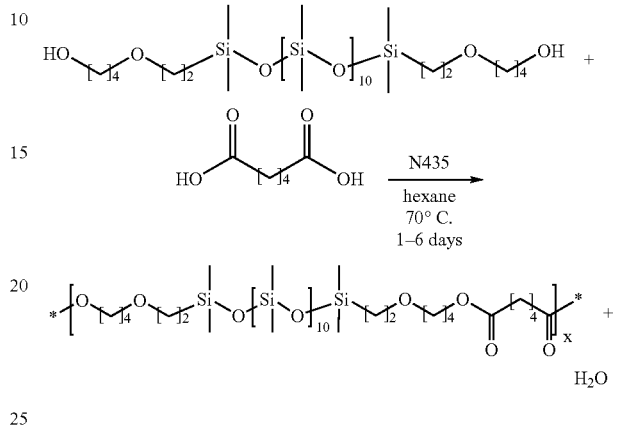

The reaction was conducted with constant stirring (i.e. magnetic stir bar) in a two-neck round-bottom flask attached to a Dean-Stark trap and a water-cooled condenser in a heated oil bath. The reaction was formulated with organosilicon:organic and solvent:monomer mole ratios equal to 1:1 and 10:1, respectively. The enzyme:monomer weight ratio was 1:10. The use of a Dean-Stark trap further promoted the esterification reaction.

Figure 8:
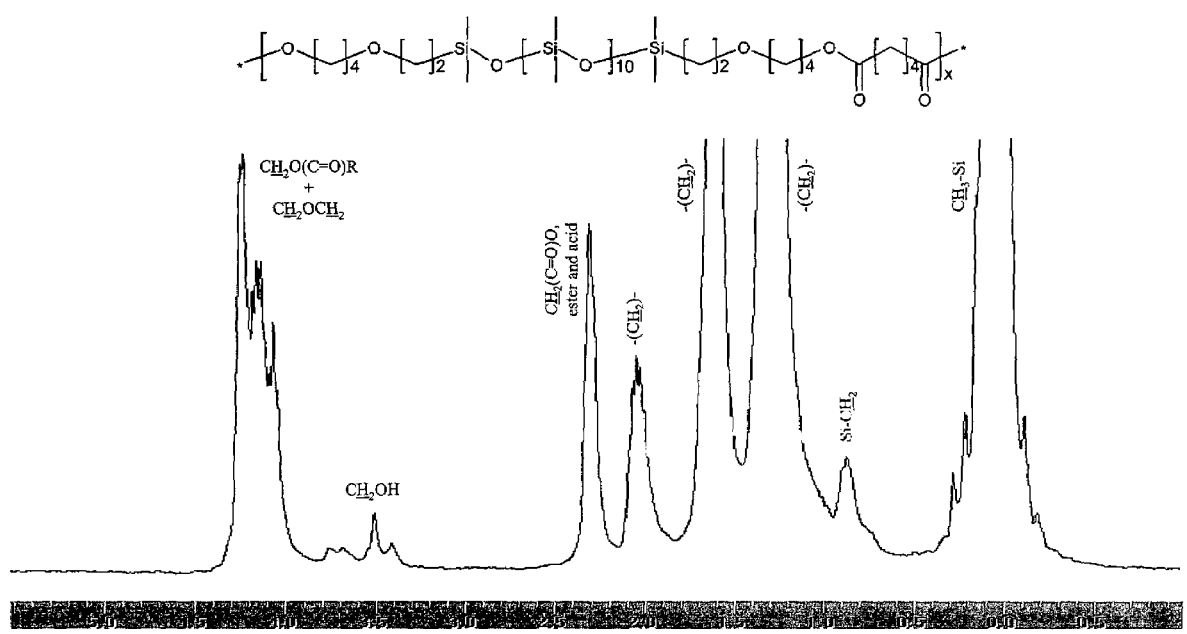
FIG. 8 is $^1H$ NMR spectrum of the esterification of Example 6.

The progress of the diol PDMS esterification was monitored by ¹H NMR. After 4 days of reaction, chloroform (~10 mL) was added to the mixture to remove the contents from the flask and filter out the enzyme. Subsequently, the filtrate was evaporated on a rotary evaporator and dried in a vacuum oven overnight at ~45° C. in order to isolate the product. The material was characterized by ¹H NMR and FTIR. FIG. 8 illustrates the ¹H NMR of the esterification. Based on the spectral data, N435 was observed to catalyze the formation of ester bonds (i.e., -[BBAA]$_x$-) with a carbinol-functional PDMS substrate.

EXAMPLE 7

N435 was used to catalyze the polyesterification of the diol PDMS (BB) and an acid-endcapped polyethylene glycol (AA) in refluxing hexane at 70° C. for 6 days as shown below:

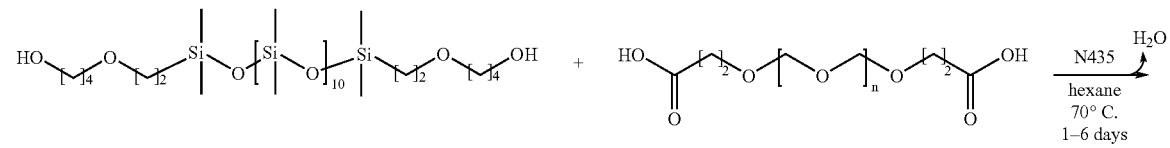

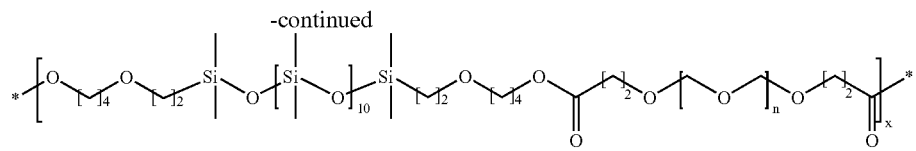

The reaction was conducted with constant stirring (i.e. magnetic stir bar) in a two-neck round-bottom flask attached to a Dean-Stark trap and a water-cooled condenser in a heated oil bath. The reaction was formulated with organosilicon:organic and solvent:monomer mole ratios equal to 1:1 and 10:1, respectively. The enzyme:monomer weight ratio was 1:10. The use of the Dean-Stark trap further promoted the esterification reaction.

After 4 days of reaction, the mixture was filtered, evaporated, and dried to isolate the product. The material was characterized by $^1$H NMR, ESI MS, MALDI-TOF MS, and GPC-RI. N435 was observed to catalyze the formation of ester bonds with large polymeric substrates. The organosilicon polyester material was also observed to contain residual reactants. Based on the GPC-RI results, the Mn and Mw values were 5500 and 19000, respectively, with a 5.4 polydisperity.

EXAMPLE 8

N435 lipase-catalyzed organosilicon polyester terpolymers were synthesized by reacting either the diacid disiloxane or diacid PDMS (x) with hexanediol (y) and adipic acid (z) in refluxing hexane or neat at 70° C. for 4 days. The diagram below shows lipase-catalyzed diacid disiloxane (A) and diacid PDMS (B) polyester terpolymers.

PDMS-functional terpolymers were calculated to be 3500–3700, 14000–15000, and 3.8–6.8 at x:y:z equal to 1:2:1, and 3200–4900, 20000–22000, and 4.0–6.8 at x:y:z equal to 0.5:2:1.5.

Based on the thermal analysis of the 0.5x:2y:1.5z terpolymers, the diacid disiloxane-(A) and diacid PDMS-(B) polyester terpolymers experienced critical mass losses at 353° C. vs. 226° C. (diacid disiloxane reactant) and 393° C. vs. 283° C. (diacid PDMS reactant), respectively. The temperature was observed to increase with the increase in organosilicon concentration. The Tg values were measured to be −76° C. (A) and −117° C. (B). In comparison to the diacid disiloxane (Tg=−76° C.) and diacid PDMS (Tg=−119° C.) reactants, similar amounts of energy were required to achieve molecular motion. During the DSC heating cycles, cold crystallization and crystalline phases were observed at −45° C. (Tcc, 2.7 J/g), −1° C. (Tm, 17.8 J/g), and 35° C. (Tm, 2.8 J/g) in terpolymer A. A cold crystallization (Tcc=−15° C., 50.4 J/g) and two crystalline phases (Tm=30° C., 45 J/g; 46° C., 8.6 J/g) were detected in the diacid disiloxane. Cold crystallization (Tcc=−101° C., 0.3 J/g) and multiple crystalline phases (Tm=−46° C. & −28° C., 14.6 J/g; 42° C. & 53° C., 0.7 J/g; 91° C., 0.9 J/g) were observed in terpolymer B. A crystalline phase (Tm=−60° C., 16.8 J/g) was detected in the diacid PDMS. Given the range of energy values, the size of

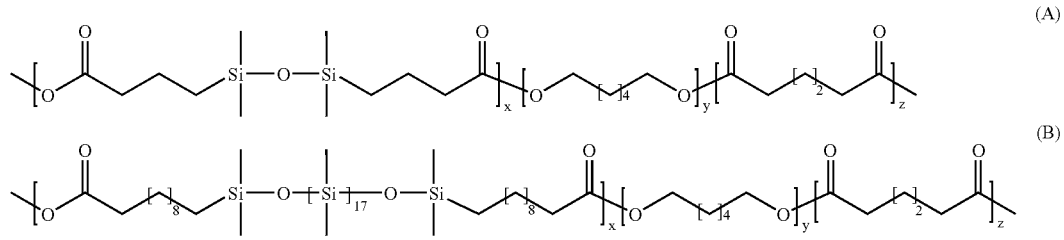

The reactions were conducted with constant stirring (i.e. magnetic stir bar) in a two-neck round-bottom flask attached to a Dean-Stark trap and a water-cooled condenser in a heated oil bath. The stoichiometry of the reactions were formulated with diacid:diol and solvent:monomer mole ratios equal to 1:1 (i.e. 1:2:1 and 0.5:2:1.5 x:y:z mole ratios) and 10:1, respectively. The enzyme:monomer weight ratio was 1:10. The use of a Dean-Stark trap further promoted the esterification reaction.

Figure 9:
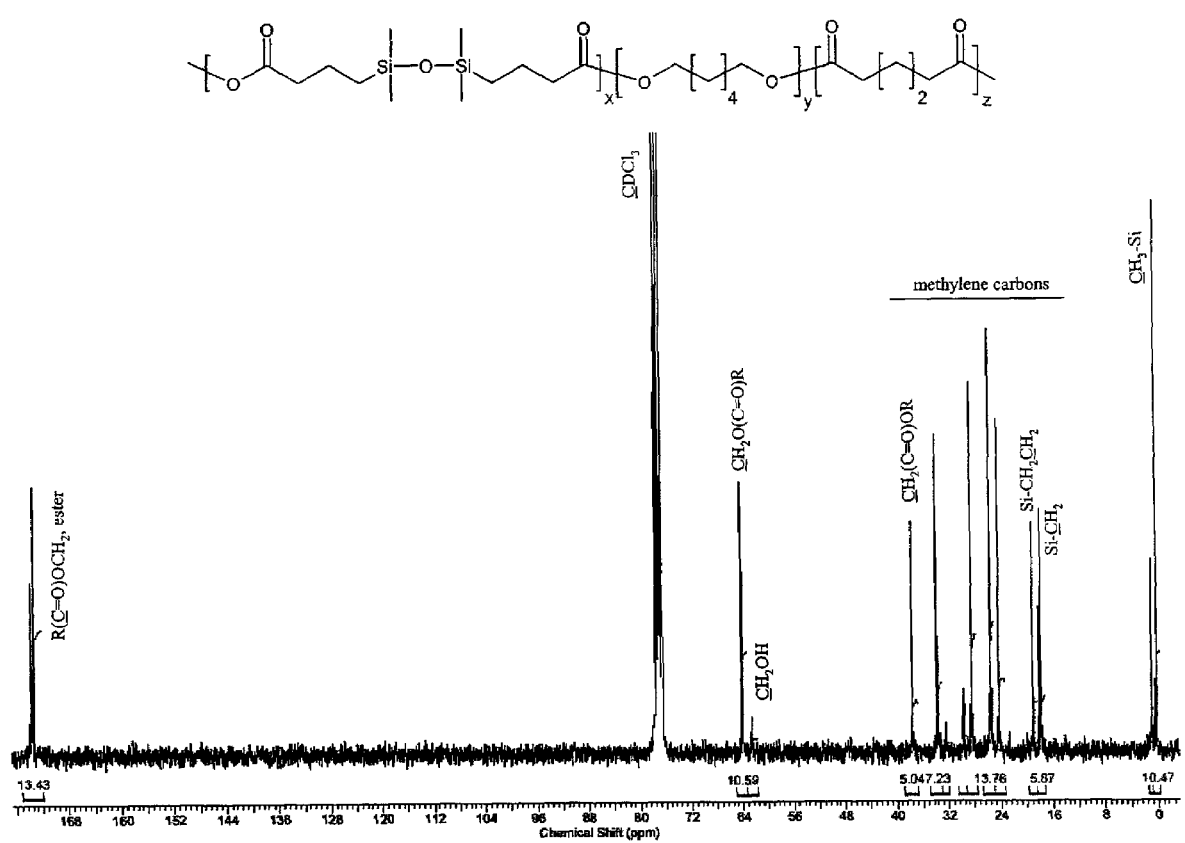
FIGS. 9–10 are $^{13}C$ DEPT NMR spectrum of the esterification of Example 8.
Figure 10:
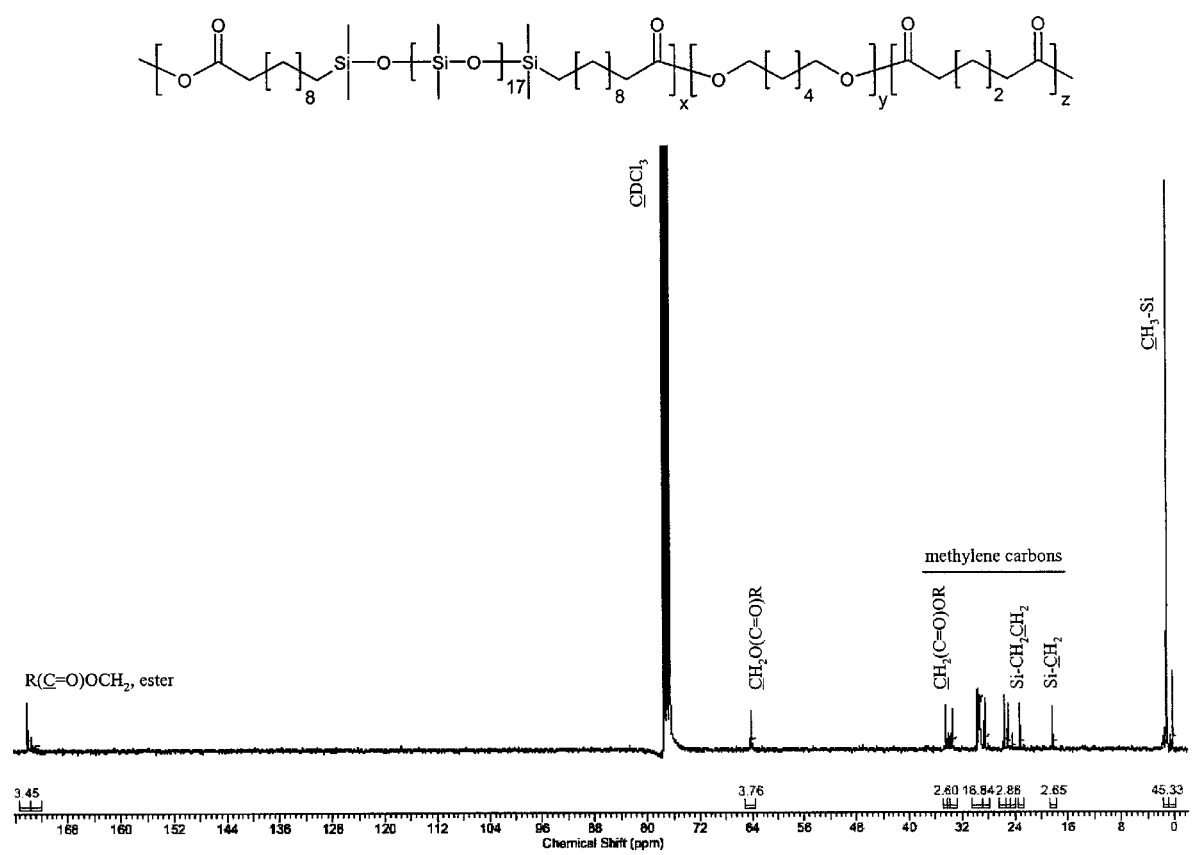

The progress of the reactions were monitored daily by $^1$H NMR. After 4 days, the mixtures were filtered, evaporated, and dried to isolate crude oily products. The materials were characterized by $^1$H, $^{13}$C, and $^{29}$Si NMR, FTIR, GPC-RI, GPC-MALS, TGA, and DSC. FIGS. 9–10 illustrate the $^{13}$C NMR analyses of the esterification. Based on the material characterization, the diacid molecules were consumed during the lipase-catalyzed esterification reactions. The Mn, Mw, and polydispersity values of the disiloxane- and the regions of order or the degree of molecular interactions varied throughout the materials.

EXAMPLE 9

Subtilisin (i.e., a protease) was used to catalyze the formation of an amide bond between trimethylsilylpropionic acid and hexyl amine as shown in the following diagram:

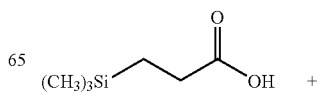

-continued

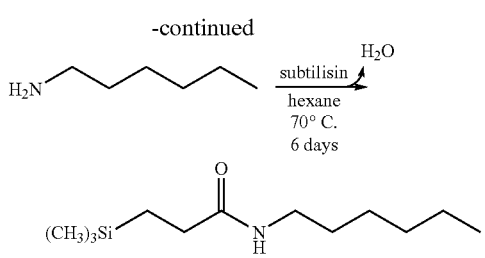

The reaction was conducted using hexane as a solvent. The reaction was conducted with constant stirring (i.e. magnetic stir bar) in a two-neck round-bottom flask attached to a Dean-Stark trap and a water-cooled condenser in a heated oil bath.

The hexane reaction was formulated with organosilicon:organic and solvent:monomer mole ratios equal to 1:1 and 10:1, respectively. The enzyme:monomer weight ratio was 1:10. The protease formed a heterogeneous suspension in the stirred organic mixture.

The hexyl amine was added to the trimethylsilylpropionic acid at 70° C. After homogenization, dried subtilisin was added to the reaction mixture and heated for 12 hours. The refluxing reaction in hexane was conducted at 70° C. for 6 days. The completion of the reaction was monitored by $^1$H NMR or thin layer chromatography (TLC).

After the reaction, chloroform was added to the mixture to remove the contents from the flask and filter out the enzyme. Subsequently, the filtrate was evaporated on a rotary evaporator and dried in a vacuum oven overnight at −45° C. in order to isolate the product. The reaction was characterized by $^{13}$C NMR. Based on the spectral results, subtilisin was observed to catalyze the formation of an amide bond. The yield was estimated to be approximately 20%.

EXAMPLE 10

Subtilisin was used to catalyze the formation of amide bonds between 1,3-bis(3-aminopropyl)-tetramethyldisiloxane (i.e. diamine disiloxane) and octanoic acid as shown in the following diagram:

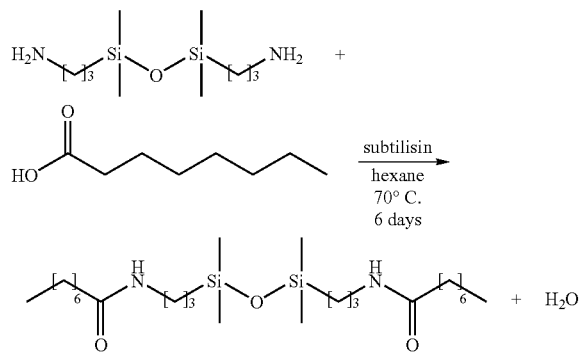

The reaction was conducted using hexane as a solvent. The reaction was conducted with constant stirring (i.e., magnetic stir bar) in a two-neck round-bottom flask attached to a Dean-Stark trap and a water-cooled condenser in a heated oil bath.

The hexane reaction was formulated with organosilicon:organic and solvent:monomer mole ratios equal to 1:1 and 10:1, respectively. The enzyme:monomer weight ratio was 1:10.

The octanoic acid was added to the 1,3-bis(3-aminopropyl)-tetramethyldisiloxane at 70° C. After homogenization, dried subtilisin was added to the reaction mixture and heated for 12 hours. The refluxing reaction in hexane was conducted at 70° C. for 6 days. The completion of the reaction was monitored by $^1$H NMR or TLC.

After the reaction, chloroform was added to the mixture to remove the contents from the flask and filter out the enzyme. Subsequently, the filtrate was evaporated on a rotary evaporator and dried in a vacuum oven overnight at ~45° C. in order to isolate the product. The reaction was characterized by $^{13}$C NMR. Based on the spectral results, subtilisin was observed to catalyze the formation of an amide bond. The yield was estimated to be approximately 20%.

EXAMPLE 11

Lipase (N435) was used to catalyze the reaction of 3-aminopropyltris(trimethyl-siloxy)silane and phenyl acetic acid methyl ester as shown in the following diagram:

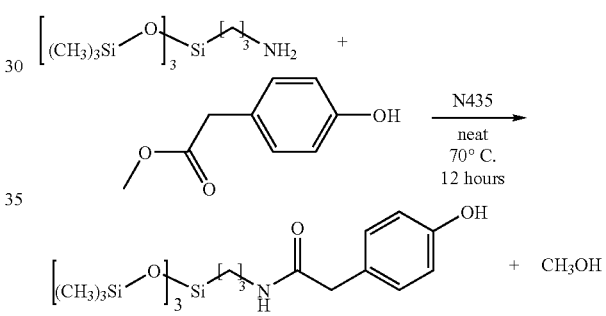

The reaction was conducted with constant stirring (i.e., magnetic stir bar) in a two-neck round-bottom flask attached to a Dean-Stark trap and a water-cooled condenser in a heated oil bath. The reaction was formulated with a organosilicon:organic mole ratio equal to 1:1. The enzyme:monomer weight ratio was 1:10. The phenyl acetic acid methyl ester was added to 3-aminopropyltris(trimethyl-siloxy)silane at 70° C. After homogenization, dried lipase enzyme was added to the reaction mixture and heated for 12 hours.

The reaction was monitored by TLC. After 12 hours, chloroform was added to the mixture to remove the contents from the flask and filter out the enzyme. Subsequently, the filtrate was evaporated on a rotary evaporator and dried in a vacuum oven overnight at ~45° C. in order to isolate the product.

Figure 11:
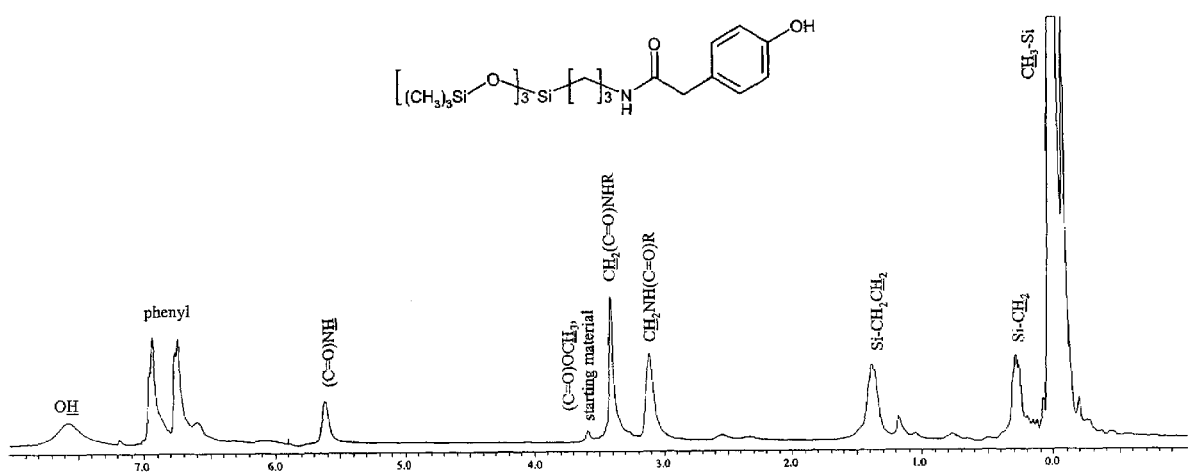
FIG. 11 is a $^1H$ NMR spectrum of the amidation of Example 11.

The material was characterized by $^1$H and $^{13}$C NMR as well as FTIR. FIG. 11 illustrates the $^1$H NMR of the amidation. Based on the spectral data, N435 was observed to catalyze the formation of the amide bond.

EXAMPLE 12

Analogous to Nylon, diamine disiloxane and dimethyl adipate were reacted with N435 as shown in the following diagram:

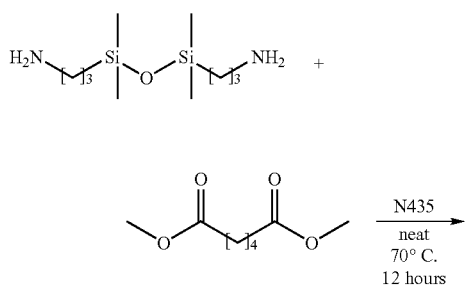

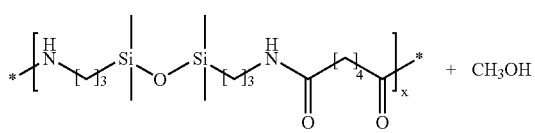

The reaction was conducted with constant stirring (i.e., magnetic stir bar) in a two-neck round-bottom flask attached to a Dean-Stark trap and a water-cooled condenser in a heated oil bath. The reaction was formulated with a orga-nosilicon:organic mole ratio equal to 1:1. The enzyme: monomer weight ratio was 1:10. The dimethyl adipate was added to diamine disiloxane at 70° C. After homogenization, dried lipase enzyme was added to the reaction mixture and heated for 12 hours.

The reaction was monitored by $^1$H NMR. After 12 hours, chloroform was added to the mixture to remove the contents from the flask and filter out the enzyme. Subsequently, the filtrate was evaporated on a rotary evaporator and dried in a vacuum oven overnight at ~45° C. in order to isolate the product.

Figure 12:
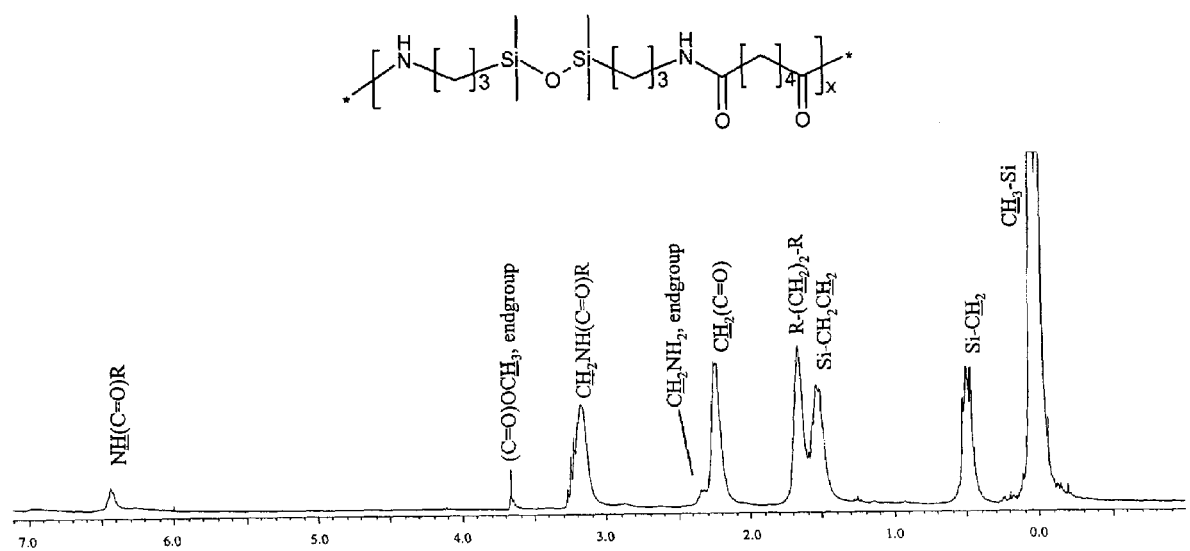
FIG. 12 is a $^1H$ NMR spectrum of the amidation of Example 12.

The material was characterized by $^1$H and $^{13}$C NMR, MALDI TOF MS, FTIR, GPC-RI, TGA, and DSC. FIG. 12 illustrates the $^1$H NMR of the amidation. Based on the molecular characterization, lipase was observed to catalyze the formation of amide bonds during the synthesis of the organosilicon polyamide. The Mn and Mw values were calculated to be 2084 and 4566, respectively, with a 2.2 polydispersity. Based on the thermal analysis, the material experienced a critical mass loss at 394° C. vs. 107° C. of diamine disiloxane. The Tg was measured to be −21° C. In comparison to the diamine disiloxane, Tg=−110° C., more energy was required to achieve molecular motion. During the first heating cycle, a crystalline phase was observed at 54° C. (Tm) with an energy equal to 9.6 J/g. No crystalline phases were observed in the diamine disiloxane. The crystalline phase provides evidence of regions of order within the material.

EXAMPLE 13

A lipase-catalyzed (N435) multifunctional organosilicon polyamide, average structure shown below, was synthesized by reacting the diacid disiloxane methyl ester with tetramine ($C_{13}H_{32}N_4$).

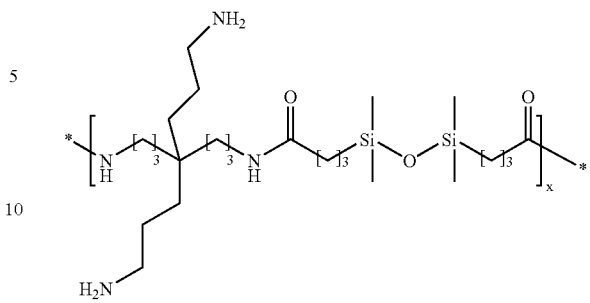

The reaction was conducted with constant stirring (i.e. magnetic stir bar) in a two-neck round-bottom flask attached to a Dean-Stark trap and a water-cooled condenser in a heated oil bath. The reaction was formulated with a orga-nosilicon:organic mole ratio equal to 1:1. The enzyme: monomer weight ratio was 1:10. The tetramine was added to diacid disiloxane at 70° C. After homogenization, dried lipase enzyme was added to the reaction mixture and heated for 24 hours.

Figure 13:
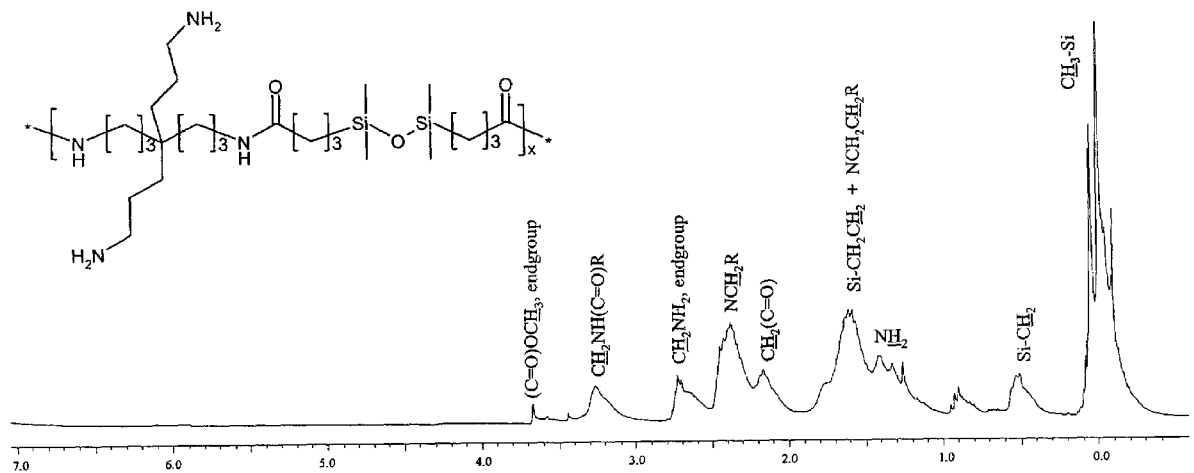
FIG. 13 is a $^1H$ NMR spectrum of the amidation of Example 13.

The reaction was monitored by $^1$H NMR. After 24 hours, chloroform was added to the mixture to remove the contents from the flask and filter out the enzyme. Subsequently, the filtrate was evaporated on a rotary evaporator and dried in a vacuum oven overnight at ~45° C. in order to isolate the product. FIG. 13 illustrates the $^1$H NMR of the amidation. Based on the spectral data, lipase was observed to catalyze the formation of amide bonds during the synthesis of the multifunctional organosilicon polyamide.

It will be obvious to those skilled in the art that various changes may be made without departing from the scope of the invention, which is not to be considered limited to what is described in the specification.

What is claimed is:

1. An organosilicon ester comprising a structurally defined compound having the formula:

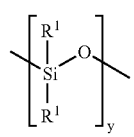

wherein:
each R' is independently selected from alkyl, haloalkyl, unsaturated alkyl, aryl, hydroxy, alkoxy, hydrogen, —$(OSiR^1_2)_x$—$OSiR^1_3$, or R'";
at least one of $R^1$=R'";
y is equal to or greater than 3; and
R'" is:

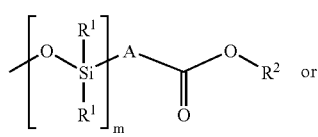

-continued

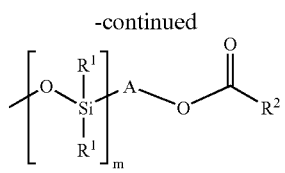

wherein:
A is a substituted or unsubstituted hydrocarbon substituent, wherein said hydrocarbon may be substituted such that said hydrocarbon comprises a halogen-, ether-, alkoxy-, phenyl-, or unsaturated-functional hydrocarbon and combinations thereof;

$R^2$ is an organic compound; and m is greater than 0.

2. The organosilicon ester as claimed in claim 1 wherein x is between 0 and about 250.

3. The organosilicon ester as claimed in claim 1 wherein A is a $C_3$ to $C_{20}$ hydrocarbon.

4. The organosilicon ester as claimed in claim 1 wherein y is between about 3 to about 6.

5. The organosilicon ester as claimed in claim 1 wherein m is greater than 0 and less than about 250.

* * * * *

UNITED STATES PATENT AND TRADEMARK OFFICE
CERTIFICATE OF CORRECTION

PATENT NO.      : 7,205,373 B2                                    Page 1 of 1
APPLICATION NO. : 10/642098
DATED           : April 17, 2007
INVENTOR(S)     : Brandstadt et al.

It is certified that error appears in the above-identified patent and that said Letters Patent is hereby corrected as shown below:

Col. 22, line 53, "each R' is" should read -- each $R^1$ is --.

Signed and Sealed this

Sixteenth Day of October, 2007

JON W. DUDAS
*Director of the United States Patent and Trademark Office*